United States Patent [19]
Broberg et al.

[11] Patent Number: 5,916,583
[45] Date of Patent: Jun. 29, 1999

[54] PRECIPITATION OF ONE OR MORE ACTIVE COMPOUNDS IN SITU

[75] Inventors: Fredrik Broberg, Trosa; Arne Brodin, Södertälje; Lisbet Rydhag, Enhörna, all of Sweden; Sylvan G. Frank, Columbus, Ohio

[73] Assignee: Astra Aktiebolag, Sodertalje, Sweden

[21] Appl. No.: 08/563,880

[22] Filed: Nov. 21, 1995

Related U.S. Application Data

[63] Continuation of application No. 08/087,504, Jul. 2, 1993, abandoned.

[30] Foreign Application Priority Data

Jul. 9, 1992 [SE] Sweden .................................. 9202128

[51] Int. Cl.$^6$ ...................................................... A61K 9/08
[52] U.S. Cl. ......................... 424/426; 424/422; 424/423; 514/818; 514/817
[58] Field of Search .................................. 424/422, 423, 424/426, 428; 514/818, 817

[56] References Cited

U.S. PATENT DOCUMENTS

| | | | |
|---|---|---|---|
| 4,259,331 | 3/1981 | Armstrong | 424/227 |
| 4,268,495 | 5/1981 | Muxfeldt et al. | 424/1 |
| 5,051,257 | 9/1991 | Pietronigro | 424/423 |
| 5,096,926 | 3/1992 | Fiorini et al. | 514/569 |
| 5,324,519 | 6/1994 | Dunn et al. | 424/426 |

FOREIGN PATENT DOCUMENTS

| | | |
|---|---|---|
| 9000634 | 3/1990 | Denmark . |
| 0197308 | 10/1986 | European Pat. Off. . |
| 0213851 | 3/1987 | European Pat. Off. . |

OTHER PUBLICATIONS

Bourget et al., "Factors Influencing Precipitation . . . " J.Clin.Pharm. and Thera. (1990) 15, 197–204.

Sinclair et al., "Topical Anesthesia with Lidocaine . . . " Anesthesiology, 68: 895–901, 1988.

Hussain et al., "Injectable Suspensions for Prolonged . . . " Drug Devel. and Ind. Pharm., 17(1), 67–76 (1991).

Holst et al., "Effects of Lidocaine aerosol . . . " Acta.Anaesthesiol.Scand. 1992: 36: 112–114.

Hoefflin, "Marcaine Spray" Plast.Reconstr.Surg., 1989: 84, 543.

J.A. Fonte Itaracs, "Bupivacaine Squirting" Ann. R. Coll. Surg. Engl. 71, 1989, 72.

Benzon et al., "The Effect of Polyethylene Glycol . . . " Anesth. Analg., 1987; 66; 553–559.

Primary Examiner—Thurman K. Page
Assistant Examiner—James M. Spear
Attorney, Agent, or Firm—White & Case L.L.P.

[57] ABSTRACT

The present invention relates to an injectable solution for administration of one or more active compounds. According to the invention the active compound, which is in its neutral form, is dissolved in a biologically acceptable solvent whereby the active compound by administration precipitates, forming a solid phase of the solution in situ. Thus, said solution, which is easy to sterilize, is acting like a suspension when injected.

11 Claims, No Drawings

PRECIPITATION OF ONE OR MORE ACTIVE COMPOUNDS IN SITU

This application is a continuation of application Ser. No. 08/087,504, filed Jul. 2, 1993 now abandoned.

FIELD OF THE INVENTION

The present invention is directed to an injectable solution for administration of one or more active compounds and a process for the preparation thereof.

BACKGROUND OF THE INVENTION

Sterile suspensions, i.e. formulations containing at least two phases, a solid and a liquid phase, are difficult to manufacture in large scale. Suspensions are by definition thermodynamically unstable, and separation of the different phases will occur with time. Steam sterilization of such formulations often speeds up the separation. Aseptic preparation by filtration through a 0.2 $\mu$m filter is not applicable on suspensions. There are few suspension products on the market of this type. Novalucol® and Roxiam® are examples of mixtures for oral administration. Oil containing suspensions for injection are available for CNS indications. There is a need for an injectable suspension which can be sterilized either by steam sterilization or by filtration through a 0.2 $\mu$m filter.

PRIOR ART

In NL 9000634 stable aqueous suspensions of water-soluble local anaesthetics and/or narcotic analgesics are disclosed where the local anaesthetics and/or narcotic analgesics have a specific particle diameter and said aqueous suspensions also containing a non-ionic surface-active agent. These suspensions are being sterilized by steam sterilization or with the aid of gammarays. When sterilized by heating the suspended particles melt and wholly or partly flow together. To obtain the suspension again the residence is cooled down to a temperature below the freezing point of the aqueous medium while shaking. However, this is a complicated way of sterilizing, it takes time and it is not possible to control the sizes of the particles recovered.

Also in EP 197 308 a ready made suspension including a water insoluble local anesthetics for injection is disclosed. During steam sterilization of the suspension the same problem as mentioned above arises, i.e. the particles of the local anesthetic melts and have to be resuspended.

EP 213 851 discloses injectable semi-solid matrices, which mechanically hinder the release of the active compound. In fact, it is the matrix that will be degraded once injected. Also the formulation here is semi-solid and not solid.

It is well-known that solutions can be obtained by chelation with metal ions. This is disclosed in e.g. U.S. Pat. No. 4,259,331. Here the mixed metal chelate releases an amount of active compound by injection. However it is desirable to prepare an injectable solution not including metal ions, but which solution still precipitates the active compound once injected.

Further in Dialog International Services, file 5:B10SIS, Benzon et al present a study concerning the effect of polyethylene glycol (PEG) on mammalian nerve impulses. PEG is a polymeric compound used as a vehicle for depot steroid preparations. According to the study, PEG in a concentration of up to 40% does not cause neurolysis.

Another way of controlling postoperative pain is described by Cassuto et al in Anaesthesiology 895, 68, 1988, namely the administering of Xylocaine® spray, i.e. a solution if lidocaine base in ethanol, topically in surgical wounds of patients undergoing hermiorraphy.

Also in Acta Anaesthesiol Scand 112–114, 36, (1992) the use of the same lidocaine aerosol is described for post-operative pain following minor gynaecological laparotomy. The base form of lidocaine which is used in both these two studies is available in vivo, i.e. the solubility in the tissue fluids is high enough to give both sensory and motor block. This is also confirmed by the present invention. Xylocaine® spray used in the earlier studies contains, however, a number of additives, which should be avoided in wounds.

In J. Clin. Pharm. and Therap. 197–204, 15, 1990 and in a report called "Slow-release effect of pH-adjusted bupivacaine, in vitro demonstration" Bourqet et al and Bonhomme et al described studies of the slow-release effect of alkalinized bupivacaine hydrochloride solutions. Further, in Correspondance in Plast. Reconstr. Surg. 543, 84, 1989 and in Comment in Ann. R. Coll. Surg. Engl. 17, 72, 1989 the possibility to administer alkanized bupivacaine hydrochloride solutions topically to control post-operative pain has been pointed out.

Slow-release of analgetics have also been observed for base forms of analgetics such as nalbuphine in Drug Devel and Ind Pharm 67, 17, 1991, where it is described how suspensions of nalbuphine are prepared and injected. To be able to prepare an injectable suspension three suspending agents, methylcellulose, sodium carboxymethyl-cellulose, and PEG are added. However, these agents give possible side-effects and therefore a suspension containing as few auxiliaries as possible is desirable.

None of the prior art documents solves the problem how to prepare a stable injectable suspension of an active agent, where said suspension has the advantage that the effect thereof is much prolonged. According to present invention said problems can be solved.

Outline of the invention

It has been found that the difficulties of preparing sterile suspensions for injection can be avoided by preparing an injectable solution for administration of one or more active compounds dissolved in a biologically acceptable solvent whereby the active compound upon administration precipitates, due to changes of the conditions of solubility, i.e. the solid phase of the suspension is formed in situ. Sterilization of a solution can be performed by methods not applicable on suspensions namely by steam sterilization or by filtration through a 0.2 $\mu$m filter.

Another advantage with the present invention is that the active compound precipitates in situ, i.e. the solid phase might also act as a depot in the tissue, due to its solubility properties or the presence of other materials (excipients). Consequently, large doses of the active compound can be administered in vivo, without obtaining severe toxic reactions. The present invention discloses an injectable solution where the active compound could be e.g. a local anaesthetic agent, an analgesic agent or a combination of these two agents giving both an analgesic and an anaesthetic effect, which sometimes is desirable. The active compound could also be a steroid or a drug for CNS indications.

The active compound is preferably a local anaesthetic agent such as lidocaine, prilocaine, mepivacaine, bupivacaine, ropivacaine or etidocaine but it can also be some other local anaesthetic agent. Most preferably the active compound is lidocaine.

The physico-chemical properieties of the active compound, i.e. solubility, the influence of pH, salts and temperature on the solubility, are important parameters to control the precipitation of the active compound in situ.

The local anaesthetic agent used according to the present invention is in its neutral form which is less soluble than the hydrochloride form. It has been found that the neutral form of the anaesthetic agent enhances the duration of motor and sensory block compared to a solution of said anaesthetic agent in hydrochloride form.

Since the neutral form is not soluble in water a lipophilic vehicle was determined which dissolves the active compound and thus made it suitable for injection. Upon administration this solution, i.e. the active compound and the vehicle, is changed due to changes of the conditions resulting in precipitation of the active compound. Thus the injectable system acts as if it was a suspension. The neutral form is unchanged and can be e.g. the base form.

The optimal vehicle for a specific active compound according to present invention, is determined experimentally and the function confirmed in vivo. The physico-chemical properties of the active compound determines the solubility of the active compound. The lower limit of solubility is determined by the lowest effective concentration of the active compound (therapeutic concentration). The upper limit of the solubility should be equal to the desired amount of precipitated active compound.

The vehicles are biologically acceptable solvents and a mixture of one or more of water, an alcohol and a polyethylene glycol or another biologically acceptable solvent. Especially preferred vehicles according to the invention are:
a) ethanol, 99.5%
b) a mixture of ethanol and water
c) polyethylene glycol 300 (PEG 300)
d) a mixture of PEG 300 and ethanol
e) a mixture of PEG 300, ethanol and water
f) polyethylene glycol 400 (PEG 400)
g) a mixture of PEG 400 and ethanol
h) a mixture of PEG 400, ethanol and water
i) propylene glycol
j) a mixture of propylene glycol and water
k) a mixture of propylene glycol and ethanol
l) glycerol
m) a mixture of glycerol and ethanol or
n) a mixture of glycerol, ethanol and water
Most preferably the biologically acceptable solvent is
a) a mixture of ethanol and water
b) PEG 300 or
c) a mixture of PEG 400 and ethanol According to an especially preferred embodiment of the invention the sterile injectable solution contains 5–80 w/w % of lidocaine dissolved in a mixture of 10–35 w/w % of ethanol and 2–65 w/w % of water.

According to a another preferred embodiment of the invention the sterile injectable solution contains 15–20 w/w % of lidocaine dissolved in 80–85 w/w % of PEG 300.

According to a further preferred embodiment of the invention the sterile injectable solution contains 5–20 w/w % of lidocaine dissolved in in a mixture of 2–10 w/w % of ethanol and 75–90 w/w % of PEG 400.

The injectable sterile solution according to present invention can be administered intramuscularly, epidurally, spinally, intratechally, rectally, topically, orally or in the lung.

The sterile injectable solution is prepared by mixing the specific active compound with the solvent in a flask. The flask is sealed and then shaken to solve the active compound. To completely dissolve the active compound, the flask is left at room temperature for one day maximum. After that the solution is sterilized either by steam sterilization or prepared aseptically and filtered through a 0.2 µm filter.

The following examples illustrate the invention more in detail

EXAMPLE 1

| | |
|---|---|
| Lidocaine | 5.0% by weight |
| Ethanol, 99.5% | 34.0% by weight |
| Water | 61.0% by weight |

A sterile injectable solution was prepared in accordance with the general preparation procedure above. A long duration of motor and sensory block was obtained when injected in vivo.

EXAMPLE 2

| | |
|---|---|
| Lidocaine | 10.0% by weight |
| Ethanol, 99.5% | 36.0% by weight |
| Water | 54.0% by weight |

A sterile injectable solution was prepared in accordance with the general preparation procedure above. A long duration of motor and sensory block was obtained when injected in vivo.

EXAMPLE 3

| | |
|---|---|
| Lidocaine | 75.0% by weight |
| Ethanol, 99.5% | 20.0% by weight |
| Water | 5.0% by weight |

A sterile injectable solution was prepared in accordance with the general preparation procedure above.

EXAMPLE 4

| | |
|---|---|
| Lidocaine | 80.0% by weight |
| Ethanol, 99.5% | 15.0% by weight |
| Water | 5.0% by weight |

A sterile injectable solution was prepared in accordance with the general preparation procedure above.

EXAMPLE 5

| | |
|---|---|
| Lidocaine | 17.8% by weight |
| PEG 300 | 82.2% by weight |

A sterile injectable solution was prepared in accordance with the general preparation procedure above.

EXAMPLE 6

| | |
|---|---|
| Lidocaine | 8.6% by weight |
| Ethanol, 99.5% | 3.4% by weight |
| PEG 400 | 88.0% by weight |

A sterile injectable solution was prepared in accordance with the general preparation procedure above. A long duration of motor and sensory block was obtained when injected in vivo.

EXAMPLE 7

| | |
|---|---|
| Lidocaine | 17.4% by weight |
| Ethanol, 99.5% | 3.4% by weight |
| PEG 400 | 79.2% by weight |

A sterile injectable solution was prepared in accordance with the general preparation procedure above. A long duration of motor and sensoric block was obtained when injected in vivo.

EXAMPLE 8

| | |
|---|---|
| Prilocaine | 10.0% by weight |
| Ethanol, 99.5% | 35.0% by weight |
| Water | 55.0% by weight |

A sterile injectable solution was prepared in accordance with the general preparation procedure above.

EXAMPLE 9

| | |
|---|---|
| Prilocaine | 20.0% by weight |
| PEG 300 | 80.0% by weight |

A sterile injectable solution was prepared in accordance with the general preparation procedure above.

EXAMPLE 10

| | |
|---|---|
| Prilocaine | 10.0% by weight |
| Ethanol, 99.5% | 5.0% by weight |
| PEG 400 | 85.0% by weight |

A sterile injectable solution was prepared in accordance with the general preparation procedure above.

EXAMPLE 11

| | |
|---|---|
| Prilocaine | 15.0% by weight |
| Ethanol, 99.5% | 5.0% by weight |
| PEG 400 | 80.0% by weight |

A sterile injectable solution was prepared in accordance with the general preparation procedure above.

EXAMPLE 12

| | |
|---|---|
| Mepivacaine | 7.7% by weight |
| Ethanol, 99.5% | 50.0% by weight |
| Water | 42.3% by weight |

A sterile injectable solution was prepared in accordance with the general preparation procedure above.

EXAMPLE 13

| | |
|---|---|
| Mepivacaine | 10.0% by weight |
| Ethanol, 99.5% | 60.0% by weight |
| Water | 30.0% by weight |

A sterile injectable solution was prepared in accordance with the general preparation procedure above.

EXAMPLE 14

| | |
|---|---|
| Bupivacaine | 1.1% by weight |
| Ethanol, 99.5% | 37.5% by weight |
| PEG 400 | 30.0% by weight |
| Water | 31.5% by weight |

A sterile injectable solution was prepared in accordance with the general preparation procedure above.

EXAMPLE 15

| | |
|---|---|
| Bupivacaine | 1.1% by weight |
| Ethanol, 99.5% | 49.6% by weight |
| PEG 400 | 49.3% by weight |

A sterile injectable solution was prepared in accordance with the general preparation procedure above.

EXAMPLE 16

| | |
|---|---|
| Ropivacaine | 1.0% by weight |
| Ethanol, 99.5% | 48.2% by weight |
| PEG 400 | 50.8% by weight |

A sterile injectable solution was prepared in accordance with the general preparation procedure above.

EXAMPLE 17

| | |
|---|---|
| Ropivacaine | 1.0% by weight |
| Ethanol, 99.5% | 29.7% by weight |
| PEG 400 | 69.3% by weight |

A sterile injectable solution was prepared in accordance with the general preparation procedure above.

Biological effect
Material and methods

Male guinea-pigs (Dunkin-Hartley, HB Sahlins Förs öksdjursfarm, Malmö, Sweden), weighing 300–600 g, were used. The animals were housed 3 to a cage with free access to food and water.

Method 1

Sciatic nerve block. Male Guinea-pigs of the Dunkin-Hartley strain (291–563 g) were used according to a modification of the technique of Shackell described in Anesth. Analg. 20–22, 14 (1935). The hind leg was extended to the full length, and the landmark for needle insertion was located by palpation of the great trochanter of the femur head. This bony prominence together with the lateral aspect of the Os Coxa and adjacent tissues forms a well defined space in which the sciatic nerve is located. The vehicle with or without local anaesthetic was injected (0,2 ml) into this pocket. Frequency of block, time of onset, duration of motor block (hind limb paralysis) and sensory block (flexor reflex block) were measured. The period of motor block was defined as loss of weight support from the hind leg to the ability to walk. The sensory block was defined as onset of unresponsiveness to painful stimuli applied by pinching the foot-pads to the return of flexor reflex.

Results

The injectable solutions of lidocaine dissolved in mixtures of ethanol and water and the solutions of lidocaine dissolved in mixtures of ethanol and PEG 400 were compared to a reference solution containing 2%, by weight of the water soluble lidocaine hydrochloride, with regard to their ability to relieve postoperative pain. As seen from table 2, all these solutions according to the present invention giving longer durations of motor block and sensoric block compared to the reference solution.

TABLE 1

Compositions of injectable solutions of lidocaine

Composition, g/100 g

| Sample No | Lido-caine | Lidocaine HCl | Ethanol | PEG 400 | Water | pH |
|---|---|---|---|---|---|---|
| I | 5.0 | — | 34.0 | — | 61.0 | 9.5 |
| II | 10.0 | — | 36.0 | — | 54.0 | 10.3 |
| III | 8.6 | — | 3.4 | 88.0 | — | 9.2 |
| IV | 17.4 | — | 3.4 | 79.2 | — | 9.2 |
| Ref. | — | 2.0 | — | — | 98.0 | 6.8 |

TABLE 2

Durations, motor and sensoric block

| Sample No. | Conc % | Motor block minutes | Freq. | Sensor block | Freq. |
|---|---|---|---|---|---|
| I | 5.0 | >96 h | 5/6 | 160 min n = 1 >380 > 96 h n = 2 >96 h n = 2 | 5/6 |
| II | 10.0 | >24 h | 3/3 | >24 h | 3/3 |
| III | 8.6 | >24 h n = 1 131.8 ± 9.5 n = 5 | 6/6 | 121 ± 4.3 | 6/6 |
| IV | 17.4 | >120 < 24 h n = 1 >72 h n = 2 | 3/3 | >120 < 24 h | 3/3 |
| Ref. | 2.0 | 22.4 ± 3.5 | 6/6 | 13.5 ± 2 | 6/6 |

We claim:

1. A sterile injectable solution for the administration of at least one active compound selected from the group consisting of a local anesthetic agent, an analgesic and a combination of a local anesthetic and an analgesic, which solution consists essentially of a therapeutically effective amount of the active compound dissolved in a biologically acceptable solvent selected from the group consisting of an alcohol; a polyethylene glycol; a mixture of an alcohol and water; a mixture of an alcohol and a polyethylene glycol; a mixture of an alcohol, water and a polyethylene glycol; propylene glycol; a mixture of propylene glycol and an alcohol; and a mixture of propylene glycol, an alcohol and water wherein the active compound precipitates upon injection in situ.

2. A method for providing enhanced duration of effect of an active compound in a mammal which comprises administering to the mammal a solution of an effective amount of the neutral form of the active compound, selected from the group consisting of a local anesthetic agent; an analgesic; and a combination of a local anesthetic and an analgesic, in a lipophilic, biologically acceptable vehicle selected from the group consisting of an alcohol; a polyethylene glycol; a mixture of an alcohol and water; a mixture of an alcohol and a polyethylene glycol; a mixture of an alcohol, water and a polyethylene glycol; propylene glycol; a mixture of propylene glycol and an alcohol; and a mixture of propylene glycol, an alcohol and water, whereupon a depot of the active compound is formed by precipitation of the compound upon injection in situ.

3. A method for treating pain in a mammal which comprises administering to the mammal a solution of an effective amount of the neutral form of an active compound, selected from the group consisting of a local anesthetic agent; an analgesic; and a combination of a local anesthetic and an analgesic, in a lipophilic, biologically acceptable vehicle selected from the group consisting of an alcohol; a polyethylene glycol; a mixture of an alcohol and water; a mixture of an alcohol and a polyethylene glycol; a mixture of an alcohol, water and a polyethylene glycol; propylene glycol; a mixture of propylene glycol and an alcohol; and a mixture of propylene glycol, an alcohol and water, whereupon a depot of the active compound is formed by precipitation of the compound upon injection in situ.

4. The injectable solution according to claim 1 wherein the active compound is a local anesthetic agent selected from the group consisting of lidocaine, prilocaine, mepivacaine, bupivacaine, ropivacaine and etidocaine.

5. The injectable solution according to claim 4, wherein the local anesthetic agent is lidocaine.

6. The injectable solution according to claim 1 which is administered intramuscularly, epidurally, spinally, intrathecally, rectally, topically or orally.

7. The injectable solution according to claim 1 wherein the biologically acceptable solvent comprises a mixture of water, ethanol and a polyethylene glycol.

8. The injectable solution according to claim 1 or 5 wherein the biologically acceptable solvent is selected from the group consisting of a) a mixture of ethanol and water, b) PEG 300 and c) a mixture of PEG 400 and ethanol.

9. The injectable solution according to claim 1 which consists essentially of 5–80 w/w % of lidocaine, 10–35 w/w % of ethanol and 2–65 w/w % of water.

10. The injectable solution according to claim 1 which consists essentially of 15–20 w/w % of lidocaine and 80–85 w/w % of PEG 300.

11. The injectable solution according to claim 1 which consists essentially of 5–20 w/w % of lidocaine, 2–10 w/w % of ethanol and 75–90 w/w % of PEG 400.

* * * * *